United States Patent [19]

David et al.

[11] Patent Number: 4,499,758

[45] Date of Patent: Feb. 19, 1985

[54] ASSEMBLY FOR TESTING WELDABILITY OF SHEET METAL

[75] Inventors: Stan A. David, Knoxville; John J. Woodhouse, Crossville, both of Tenn.

[73] Assignee: The United States of America as represented by the United States Department of Energy, Washington, D.C.

[21] Appl. No.: 447,577

[22] Filed: Dec. 7, 1982

[51] Int. Cl.³ .................. G01L 5/04; B21J 13/08; B23Q 3/00
[52] U.S. Cl. .................... 73/159; 73/432 R; 73/864.91; 219/161; 269/288
[58] Field of Search ............ 73/159, 850, 856, 150 A, 73/432 Z, 863, 864.91; 219/158, 161; 269/287, 288

[56] References Cited

U.S. PATENT DOCUMENTS 3,050,991 8/1962 Madrzyk et al. .................. 73/856
3,321,961 5/1967 Boeuf et al. ....................... 73/856

FOREIGN PATENT DOCUMENTS 2503892 8/1975 Fed. Rep. of Germany ... 73/150 A

OTHER PUBLICATIONS

IBM Technical Disclosure Bulletin, by W. E. Milligan, vol. 13, No. 10, Mar. 1971.

Primary Examiner—Charles Frankfort
Assistant Examiner—W. Morris Worth
Attorney, Agent, or Firm—Edwin D. Grant; Stephen D. Hamel

[57] ABSTRACT

A test assembly for determining the weldability of sheet metal includes (1) a base having a flat side surface with an annular groove in the side surface, a counterbore being formed in the outer wall of the groove and the surface portion of the base circumscribed by the inner wall of the groove being substantially coplanar with the bottom of the counterbore, (2) a test disk of sheet metal the periphery of which is positioned in the counterbore and the outer surface of which is coplanar with one side of the base, and (3) a clamp ring overlying the side surface of the base and the edge portion of the test disk and a plurality of clamp screws which extend through the clamp ring for holding the periphery of the test disk against the bottom of the counterbore.

5 Claims, 2 Drawing Figures

ASSEMBLY FOR TESTING WELDABILITY OF SHEET METAL

This invention, which resulted from a contract with the United States Department of Energy, relates to an assembly for testing the susceptibility of sheet metals to crack when welded.

BACKGROUND OF THE INVENTION

The ability of thin sheets of newly developed metal alloys to remain free of cracks adjacent welds made thereon cannot conveniently be tested by test methods which have heretofore been available for this purpose. Furthermore, testing procedures which involve placing different weld patterns on sheet metal specimens which have different sizes and which are supported in different ways prevent meaningful correlation of test data.

SUMMARY OF THE INVENTION

It is therefore an object of this invention to provide an improved weldability test for sheet metal.

Another object of the invention is to provide a fixture which facilitates duplication of test conditions in the determination of the susceptibility of different sheet metal alloys to crack when welded.

These objects are attained by a preferred embodiment of the invention comprising (1) a circular base plate having an annular groove formed in one side surface thereof and a counterbore formed in the outer wall of said groove, the surface of said base plate circumscribed by said groove being coplanar with the bottom surface of said counterbore, (2) a sheet metal test disk the edge portion of which is positioned in said counterbore and the outer surface of which is coplanar with one side surface of said base plate, (3) a clamp ring overlying said one side surface of said base plate and the edge portion of said test disk, and (4) means for urging said clamp ring toward said one side surface of said base to thereby fix the edge portion of said test disk in said counterbore.

DETAILED DESCRIPTION OF THE PREFERRED EMBODIMENT OF THE INVENTION

Figure 1:
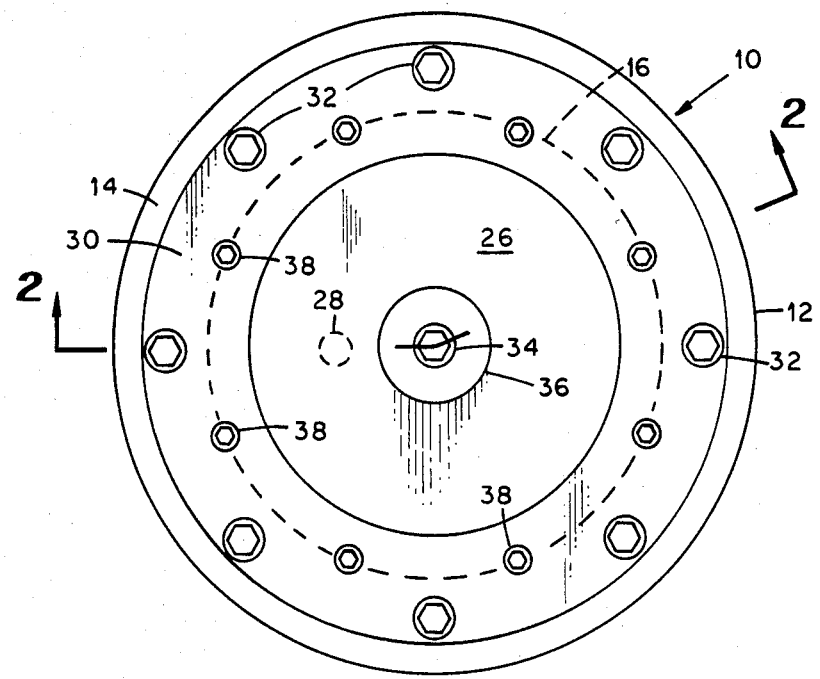
FIG. 1 is a plan view of the preferred embodiment of the invention.
Figure 2:
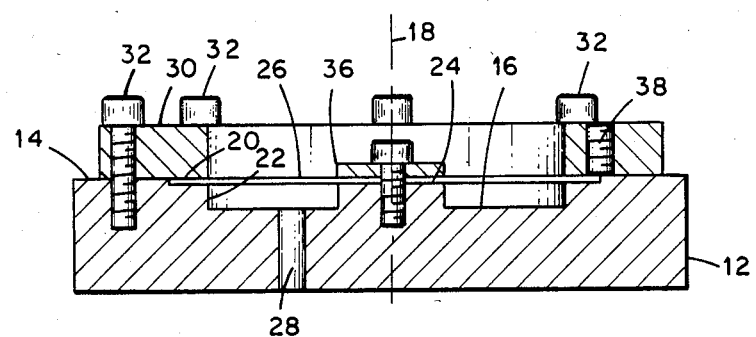
FIG. 2 is a cross section of the same embodiment of the invention, taken along the planes indicated by the broken line 2—2 in FIG. 1.

The preferred arrangement of a weldability testing assembly constructed in accordance with the principles of this invention is generally designated by reference number 10 in FIG. 1 and comprises a circular base plate 12 which will be referred to hereinafter simply as the base of the assembly. Base 12 has a flat upper side surface 14 in which is formed a groove generally designated by reference number 16, this groove being centered on the central axis 18 of the base and having a shallow counterbore 20 in its outer side wall 22. The surface 24 of base 12 circumscribed by groove 16 is coplanar with the bottom surface of counterbore 20, and the edge portion of a sheet metal disk 26 (the test specimen) conformably fits in counterbore 20 with its outer surface even with the side surface 14 of base 12 as illustrated. A vent hole 28 extends from groove 16 to the lower surface of base 12 to permit gas flow from the groove to ambient space. The edge portion of test disk 26 is fixedly held in counterbore 20 by a clamp ring 30 which abuts the upper surface of the disk and the side surface 14 of base 12 and which is secured to the base by a plurality of bolts 32 the shanks of which respectively extend through holes spaced apart around the clamp ring and which are threaded into holes in the base (only one hole in clamp ring 30 and one hole in base 12 for a bolt 32 being illustrated, in FIG. 2). The shank of a bolt 34 extends through the aperture in a clamp washer 36 which rests on the central portion of that disk 26, through an aperture formed in the center of said disk, and into a hole formed in the center of base 12. A plurality of clamp screws 38 (only one of which is illustrated in FIG. 2) also are respectively engaged in holes spaced apart around clamp ring 30, and the ends of these screws abut the outer surface of test disk 26 at points overlying the outer side wall 22 of counterbore 20.

Operation of the Preferred Embodiment of the Invention

The procedure for testing the weldability of a specimen of sheet metal is carried out as follows. A specimen in the form of a test disk 26, which conveniently is formed with a standard diameter of 2 inches (5.08 cm) and a thickness of 0.025 inch (0.635 mm), is placed in the test assembly as illustrated in the drawings and held in position by clamp ring 30, clamp washer 36 and clamp screws 38. Two circular welds of 0.875 inch and 1.375 inch, respectively, are made on the exposed surface of the test disk by the so-called GTA (gas tungsten arc) welding process. Test disk 26 is then removed from the test assembly, turned over, and again clamped in the assembly, whereupon the weld procedure is repeated to apply GTA welds to the exposed surface of the disk directly opposite the two welds that were previously made. This welding procedure subjects the test disk to heat conditions which are optimal for causing cracks to form therein. The restraint applied to the test disk 26 can be varied by clamping the disk with clamp ring 30 only, with clamp ring 30 and clamp washer 36, or with clamp ring 30, clamp washer 36 and clamp screws 38 which are flat point set screws in the preferred embodiment. However, the use of the same procedure for testing a series of sheet metal disks formed of different materials ensures that meaningful test data are obtained. If a material is subjected to welding by use of the described test assembly and does not show any cracking at or adjacent any weld, it is classified as weldable. If a circular weld of smaller diameter shows evidence of cracking and a larger weld does not, the material may be classified as one susceptible to cracking. If both smaller and larger welds show evidence of cracking, the material may be classified as one highly susceptible to cracking.

What is claimed is:

1. A test assembly for determining weldability of sheet metal, comprising:
    a base having a flat side surface, an annular groove having inner and outer walls formed in said side surface, and a counterbore having a bottom surface parallel to said side surface and an outer side wall extending between said bottom surface of said counterbore and said side surface of said base formed in the outer wall of said groove, the surface of said base circumscribed by the inner wall of said groove being substantially coplanar with the bottom surface of said counterbore;

a sheet metal test disk having an edge portion which is positioned in said counterbore and an outer surface which is substantially coplanar with said side surface of said base;

a clamp ring overlying said side surface of said base and the edge portion of said test disk; and means for urging said clamp ring toward said side surface of said base to thereby fix the edge portion of said test disk in said counterbore.

2. The test assembly of claim 1 wherein said means for urging said clamp ring toward said side surface of said base comprises a plurality of bolts having shank portions which respectively extend through holes spaced apart around said clamp ring and which are engaged in holes in said base.

3. The assembly of claim 2 wherein an aperture extends through said test disk at the center thereof and including:

a clamp washer abutting the central portion of said outer surface of said test disk; and a bolt the shank of which extends through the aperture in said clamp washer and the aperture in said test disk and which is engaged in a hole in the center of said base.

4. The assembly of claim 3 including a plurality of clamp screws respectively engaged in holes spaced apart around said clamp ring, said clamp screws abutting said outer surface of said test disk at points overlying the outer side wall of said counterbore.

5. The assembly of claim 4 wherein said base is a circular plate.

* * * * *